March 28, 1972 P. E. COSTICH Plant Pat. 3,090
DOGWOOD TREE
Filed Dec. 29, 1969
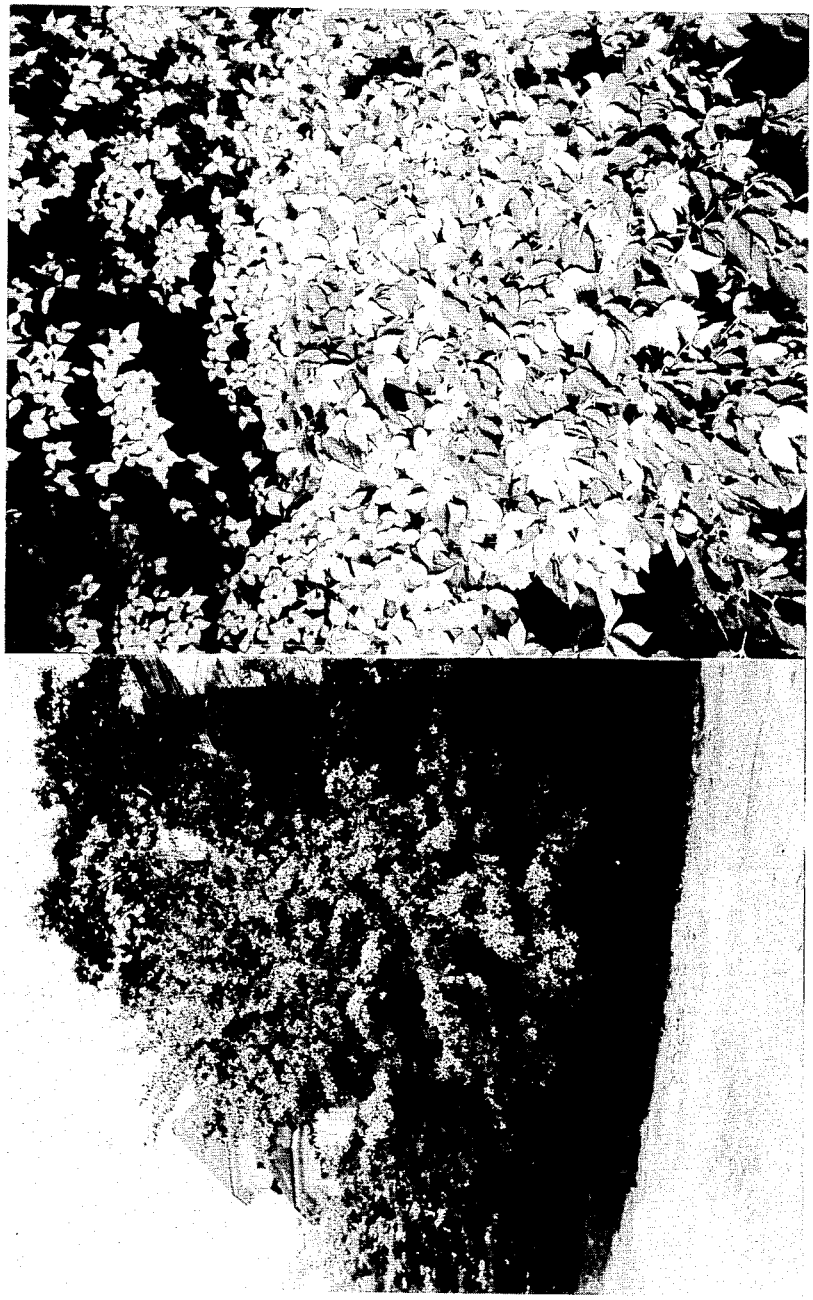
Inventor.
Peter E. Costich
By: Robb & Robb
Attorneys.

United States Patent Office

Plant Pat. 3,090
Patented Mar. 28, 1972

3,090
DOGWOOD TREE

Peter E. Costich, Center Moriches, N.Y., assignor to Treesearch, Kingston, N.J.

Filed Dec. 29, 1969, Ser. No. 889,005
Int. Cl. A01h *5/12*
U.S. Cl. Plt.—51 1 Claim

The present invention relates to a new and distinct variety of dogwood tree of the Japanese dogwood type botanically known as *Cornus kousa*, which was discovered by me in my cultivated garden located at Center Moriches, Long Island, N.Y., said new variety having originated as a newly found seedling of unknown parentage.

My attention was attracted to the new seedling by the fact that although it generally resembled the typical dogwood varieties of the species *Cornus kousa* in most respects, the flowers were at least 25% more abundant, substantially larger in size by approximately 20%, and retained their white color in unblemished condition until late August to mid-September, more than two months longer than the flowers of ordinary *Cornus kousa* varieties which usually fade in two weeks after their normal June 10 to June 15 blooming date when grown under the same conditions in the same region.

Prolonged observations and tests of the original new seedling and progeny thereof derived by twig grafting, as performed on my behalf in South Brunswick Township, N.J., have conclusively demonstrated that the aforementioned characteristics and distinctions come true and are established and transmitted through succeeding propagations, and that the new seedling is distinguished from all other dogwood varieties of which I am aware. I am, therefore, convinced that the combined flowering characteristics and habits of my new seedling as referred to in the foregoing, are unique and established it as a new and improved dogwood variety of the *Cornus kousa* species.

The accompanying drawing shows a typical tree specimen of my new variety, as well as typical foliage and flowers on a larger scale.

The following is a detailed description of my new dogwood variety, with color terminology in accordance with the Munsell Color Chart, published by Munsell Color Company, Inc., of Baltimore, Md., except where general color terms of ordinary dictionary significance are obvious:

Parentage: A newly found seedling of unknown parentage.
Propagation: Holds its distinguishing characteristics through succeeding propagations by twig grafting.
Locality where grown and observed: South Brunswick Township, N.J.
Tree: Small; spreading; hardy.
*Trunk.*—Stocky; exfoliating in patches.
*Branches.*—Slender; rough. Color—Dark Brown, Hue 7.5 YR 3/2. Lenticels—abundant.

Foliage:
*Leaves.*—Abundant; about 9.0 cm. long; about 4.5 to 5.0 cm. wide; thick and coriaceous. Shape: oval, with abruptly tapering apex. Color: upper surface—Moderate Olive Green, Hue 7.5 GY 4/4. Under surface—Moderate Yellow Green, Hue 7.5 GY 5/7. Margin: Smooth edge; undulate. Petiole: Very short. Glands: None.
Flower buds: Hardy; about 0.4 cm. long; pointed shape.
*Color.*—Dark brown when in dormant state.
Flowers:
*Dates of first and full bloom.*—About June 10 to June 15 and June 15 to 20, respectively, with flowers remaining unblemished until about Sept. 10 to 12.
*Quantity.*—Abundant; about 25% more abundant than the flowers typical of the species *Cornus kousa.*
*Size.*—Large; about 20% larger than the flowers typical of the species *Cornus kousa.*
*Petalage.*—Number of petals: 4. Shape of petals: From lance-ovate to subcordate. Size: Length—about 6.5 cm. Width—about 3.5 cm. Color: White.
Fruits:
*When borne.*—About Sept. 10 to 30.
*Abundance.*—Abundant.
*Shape.*—Globular.
*Size.*—About 2.0 cm. in diameter.
*Color.*—Dark Reddish Orange, Hue 7.5 R 4/11.
General observations: My new dogwood variety is a spectacular summer flowering tree as distinguished from normal trees of the *Cornus kousa* species which flower only in late spring or early summer.

I claim:

1. A new and distinct variety of dogwood tree of the Japanese dogwood type, substantially as herein shown and described, characterized particularly as to novelty by its general similarity to typical varieties of the species botanically known as *Cornus kousa*, but being primarily distinguished therefrom by its prolonged and spectacular summer flowering habit, with its flowers retaining their white color and remaining unblemished from about mid-June to late August or mid-September, and said flowers being about 25% more abundant in average quantity and about 20% larger in average size in comparison with the normal flowers typical of the *Cornus kousa* species which fade in about two weeks after their normal June 10 to June 15 blooming date when grown under the same conditions in the same region of Central New Jersey and Southern New York.

No references cited.

ROBERT E. BAGWILL, Primary Examiner